United States Patent [19]

Ciabatti

[11] Patent Number: 4,487,721

[45] Date of Patent: Dec. 11, 1984

[54] PROCESS FOR PRODUCING 2-AMINO-2-ARYLACETONITRILES

[75] Inventor: Romeo Ciabatti, Milan, Italy

[73] Assignee: Gruppo Lepetit S.p.A., Milan, Italy

[21] Appl. No.: 502,042

[22] Filed: Jun. 7, 1983

[30] Foreign Application Priority Data

Jun. 16, 1982 [IT] Italy .............................. 21879 A/82

[51] Int. Cl.$^3$ ........................................... C07C 121/78
[52] U.S. Cl. ........................... 260/465 E; 544/163; 544/392; 544/395; 546/230; 546/330; 548/566; 549/74; 549/491
[58] Field of Search ................. 260/465 E; 544/392, 544/395, 163; 546/230, 330; 548/566; 549/74, 491

[56] References Cited

U.S. PATENT DOCUMENTS

| | | | |
|---|---|---|---|
| 3,313,683 | 4/1967 | Taylor | 424/304 |
| 4,072,698 | 2/1968 | Hylton et al. | 260/465 E |
| 4,350,641 | 9/1982 | Degner et al. | 260/465 E |
| 4,370,493 | 1/1983 | Davis, Jr. | 260/465 E X |

OTHER PUBLICATIONS

Beilstein, 14, 462, (1931).

Primary Examiner—Dolph H. Torrence
Attorney, Agent, or Firm—William J. Stein; Stephen L. Nesbitt; Gary D. Street

[57] ABSTRACT

The present invention is directed to a process for producing 2-amino-2-arylacetonitriles of general formula I:

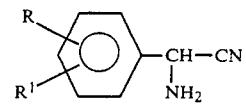

wherein R and R$^1$ independently represent hydrogen, hydroxy, hydroxy($C_1$-$C_4$)alkyl, ($C_1$-$C_4$)alkoxy, ($C_1$-$C_6$)alkyl, 2-furyl, 2-thienyl, 4-pyridinyl, 1-pyrrolydinyl, 1-piperidinyl, 4-morpholinyl, 1-piperazinyl, 4-methyl-1-piperazinyl, 4-phenylpiperazinyl, or phenyl which can optionally be substituted with from 1 to 3 substituents independently selected from ($C_1$-$C_4$)alkyl and ($C_1$-$C_4$)alkoxy, or R and R$^1$ independently represent a phenyl($C_1$-$C_4$)alkyl or a phenyl($C_1$-$C_4$)alkoxy group wherein the phenyl group can be either unsubstituted or substituted as above.

An arylaldehyde derivative of formula II

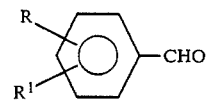

is reacted with chloroform in base and in the presence of ammonia to give the 2-amino-2-arylacetonitrile derivative.

15 Claims, No Drawings

PROCESS FOR PRODUCING 2-AMINO-2-ARYLACETONITRILES

The present invention is directed to a process for producing 2-amino-2-arylacetonitriles of general formula I:

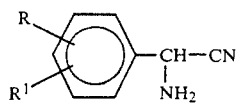

Wherein R and $R^1$ independently represent hydrogen, hydroxy, hydroxy($C_1$-$C_4$)alkyl, ($C_1$-$C_4$)alkoxy, ($C_1$-$C_6$)alkyl, 2-furyl, 2-thienyl, 4-pyridinyl, 1-pyrrolydinyl, 1-piperidinyl, 4-morpholinyl, 1-piperazinyl, 4-methyl-1-piperazinyl, 4-phenylpiperazinyl, or phenyl which can optionally be substituted with from 1 to 3 substituents independently selected from ($C_1$-$C_4$)alkyl and ($C_1$-$C_4$)alkoxy, or R and $R^1$ independently represent a phenyl($C_1$-$C_4$)alkyl or a phenyl($C_1$-$C_4$)alkoxy group wherein the phenyl group can be either unsubstituted or substituted as above. ($C_1$-$C_6$)Alkyl groups are straight or branched alkyl groups having from 1 to 6 carbon atoms, such as methyl, ethyl, 1-propyl, 2-propyl, 1-butyl, 2-butyl, 1-(2-methyl)propyl, and 2-(2-methyl)propyl, pentyl and the like. As used in describing the present invention, ($C_1$-$C_4$)alkoxy refers to straight or branched alkoxy groups of 1 to 4 carbon atoms such as methoxy, ethoxy, 1-propoxy, 2-propoxy, 1-butoxy, 2-butoxy, 1-(2-methylpropoxy), and the like while "halogen" or "halo" refers to a halogen atom selected from chlorine, bromine or iodine.

An outline of the process of the present invention is as follows:

SCHEME I

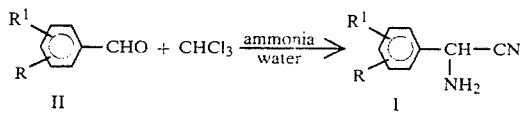

(The above equation is simply illustrative and should not be construed as indicating a balanced equation). An arylaldehyde derivative of formula II is reacted with chloroform in base and in the presence of ammonia to give a 2-amino-2-arylacetonitrile derivative.

2-Amino-2-arylacetonitriles are known as intermediates in various chemical reactions, which mainly involve the transformation of the nitrile function into other functions such as carboxy or carboxylic acid amide, ester, halide, and the like and those that can be obtained from them by known techniques.

The reactivity of the nitrile function is in fact known in the art (see for instance, Rappoport "The chemistry of the cyano groups" pp. 239-240, Interscience Publ., New York, 1970.

Many processes are known to produce 2-amino-2-arylacetonitriles. Generally they are characterized by the reaction of an arylaldehyde with a cyanide, either directly (see Beilstein 14, 462; R. Breslow, J.A.C.S., 80, 5991 (1958); and Eisenberm, Org. Prep. Proc. Int. 8n 149 (1976)) or indirectly, after having formed the corresponding methanesulphonate (see U.S. Pat. No. 3,313,683 and NL patent application No. 7311012).

The use of hydrogen cyanide in the above reaction is described for example by Lichtenberger in Bull. Soc. Chim. France, 1184 (1956). However, all these prior-art processes require the use of a cyanide which is a very hazardous material to be handled, mainly because of its high toxicity which requires special handling precautions and ad hoc apparatus, especially when considerable amounts of the substance are used, as in industrial scale productions (see for instance, N. Irwing Sax, "Dangerous Properties of Industrial Materials", p. 649, Reinhold Publishing Co., New York, Second Edition). On the contrary, the present process does not require the use of a cyanide as the starting material and is therefore more suitable than the prior-art ones for large scale productions.

As illustrated above (see Scheme I), an arylaldehyde of formula II is reacted with a molar excess of chloroform and ammonia under basic conditions.

Representative examples of basic agents capable of providing the above basic conditions are aqueous alkali metal and alkali-earth metal hydroxides such as sodium or potassium hydroxide, or ammonium hydroxide, alkali metal carbonates, and the like and mixtures thereof. The reaction can be carried out in the presence of an inert organic solvent, i.e. an organic solvent which does not unfavourably interfere with the reaction course, further characterized by being water immiscible.

A preferred embodiment of the invention is the use of an excess of chloroform as the reactant as well as the reaction solvent.

According to a preferred embodiment of the process of the invention, the process is carried out in a sealed reaction vessel such as a Parr bomb or autoclave, in order to use an excess pressure of ammonia.

According to a further preferred embodiment, the reaction is carried out under ammonia excess pressure and using aqueous ammonia as the basic agent.

Another preferred embodiment is represented by the use of gaseous ammonia in a molar excess capable of producing an overpressure of 4-10 atm. at room temperature.

The reaction temperature depends on the other reaction parameters such as the concentration of the reactants and the excess pressure applied. Generally, it ranges from 50° C. to 120° C., and preferably is between 60° and 110° C.

The reaction time can vary widely, depending on the reaction conditions. Generally, however, the reaction is complete in from 2 to 8 hours, or more. In any case, the skilled technician is able to choose the suitable reaction time under the selected conditions, for instance by sampling the reaction mixture at different times and assaying for the final product by thin layer chromatography.

The recovery of the final product is carried out according to the usual practices such as extraction with solvents, counter current extraction, precipitation by solvents, chromatographic techniques, and the like. The product can be further purified employing usual techniques such as crystallization from solvents, liquid-liquid chromatography or other chromatographic techniques.

According to the process of the invention, the best results are achieved when the final product, the alpha-amino-acetonitrile of formula I, is remarkably lypophilic in character so that it easily dissolves in chloroform or in the organic solvent which is used as the reaction solvent (if any). In so doing, the compound of formula I, the reaction product, is extracted by the chloroform or organic solvent from the basic aqueous reaction mixture, thus avoiding a prolonged contact between said product and said basic mixture which is the reaction condition favourable to the hydrolysis of the reaction product itself.

Therefore the main feature of the amino-aryl-nitriles that can be prepared according to the present invention is their lyophilic character, i.e. the water/oil partition coefficient should be more with respect to the oily phase. On the basis of the above information and of what is generally known in the art, the skilled man is able to predict the lyophilicity of the final compounds in view of the lyophilic nature of the starting aldehyde, and select the suitable starting materials and the optimal reaction conditions for carrying out the process of the present invention.

According to another preferred embodiment, when the reaction is carried out employing chloroform as the reactant as well as the solvent, i.e. without adding another organic solvent, the desired 2-amino-2-aryl-acetonitrile derivative is easily recovered by separating the organic phase and extracting it with an acidic aqueous solution.

The use of aqueous hydrochloric acid proven very efficient and, any acidic aqueous solution, in particular a mineral acid aqueous solution, can be suitably employed. The acidic layer is then neutralized and extracted with a suitable organic solvent. Representative examples of said solvents are halo($C_1$–$C_4$)alkanes such as methylene chloride, chloroform, dichloroethane, dibromoethane and the like. Preferably the pH of the aqueous phase before the extraction is between pH 7.2 and 8. The organic fractions are pooled and concentrated to a small volume under reduced pressure to precipitate the desired product. The recovered crude product is then purified according to known chromatigraphic techniques or through solubilization and subsequent precipitation by a non-solvent.

A preferred group of compounds that can be prepared by the process of the invention includes those compounds of formula I wherein $R^1$ represents hydrogen and R has one of the above represented meanings, hydrogen excluded.

Another preferred group of compounds includes those compounds of formula I wherein R is hydrogen and $R^1$ is methoxy or benzyloxy.

A preferred compound among those obtained by the process of the invention is 2-amino-2-(4-methoxyphenyl)acetonitrile.

The main use of the products obtained from the process of the present invention is as an intermediate in the synthesis of pharmacologically active substances. For instance the products can be transformed into the corresponding carboxylic acid derivative and reacted with 6-amino-penicillanic acid or 7-aminocephalosporanic acid to give semi-synthetic antibiotics that can be used as such or further transformed. Generally in the above use only one of the two enantiomers of the 2-amino-2-arylacetonitriles obtained according to the process of the present invention is desired, since only one of the enantiomers of the final compound generally possesses the desired pharmacological activity. In this case, it is desirable to resolve the two enantiomers, i.e. aminoarylnitriles, before submitting the compound to further transformation. The separation step can be accomplished according to the techniques known in the art (see "Basic principles of organic chemistry", J. Roberts and C. Caserio, W. T. Benjamin, Inc., N.Y. 1964, page 497, "Advanced organic chemistry reaction mechanism and structure", J. March, Mc Graw-Hill, 1968, page 92, "Stereochemistry of organic compounds", E. L. Eliel, Mc Graw-Hill, 1962, pages 47–85), and more particularly techniques for separating racemic aminonitriles such as those described in U.S. Pat. No. 4,072,698.

One of the main advantages of separating the enantiomers at this stage and not later is that the discarded enantiomer can easily be hydrolyzed to give the starting aldehyde, which, in turn, can be re-employed in the process of the invention. The above hydrolysis is carried out under basic conditions. The reaction temperature is generally room temperature, even if a slightly cooler temperature may be preferred at least at the beginning of the reaction. In general, higher temperatures are not necessary. If the separation of the racemic mixture is carried out at a later stage, (see Kaneko et al. "Synthetic production and utilization of aminoacids" pages 43–47, Tohn Wiley and Sons, N.Y. 1972), this very convenient recovery technique cannot be applied. The discarded enantiomer can also be epimerized to transform it into the desired one. (See U.S. Pat. No. 4,072,698).

The following examples better illustrate the present invention but should not be construed as imposing any limitation upon its overall scope.

EXAMPLE 1

2-amino-2-(4-methoxyphenyl)acetonitrile

A mixture of 4-methoxybenzaldehyde (4 g; 0.03 moles), chloroform (50 ml; 0.62 moles), 32% aqueous ammonia (50 ml; 0.83 moles), and sodium hydroxide (1.29 g; 0.03 moles) is loaded into a 1 liter Parr bomb.

The reaction vessel is closed and brought to a pressure of 3 atm. with gaseous $NH_3$ at room temperature. The reaction temperature is increase to 100° C., under stirring, and kept at this temperature for 2 hours. The Parr bomb is then cooled, the gaseous ammonia in excess is vented off and the reaction mixture is poured into a separatory funnel. The organic layer is separated and extracted with hydrochloric acid; the combined acid extracts are adjusted to pH 7.5 with aqueous sodium bicarbonate and extracted with methylene chloride. The organic layer is dried and the solvent evaporated under reduced pressure, thus obtaining the crude product of the title (2.4 g). The analytical results are in agreement with those of literature.

EXAMPLE 2

Recovery of the Unreacted Starting Aldehyde Derivative

The chloroform layer after extraction with aqueous hydrochloric acid (see example 1), is dried over sodium sulphate and concentrated under reduced pressure to obtain a residuate which, upon analysis, proves to be 4-methoxybenzaldehyde (1.83 g). This product may be further purified by column chromatography using silica gel as the adsorbent and a mixture hexane/ethyl ether in incremental proportion as the eluting mixture.

EXAMPLE 3

Resolution of the Racemic 2-amino-2-(4-methoxyphenyl)acetonitrile (Method A)

The product obtained according to example 1 (6 g; 0.037 mol) in 20 ml of benzene is added to a solution of L(+)tartaric acid (6.3 g; 0.042 mol) and acetone (2.65 g;

0.042 mol) in methanol at 40° C. under a nitrogen atmosphere. After 2 hours at 40° C. the mixture is cooled and filtered thus obtaining 9.3 g of D(-)-2-amino-2-(4-methoxyphenyl)acetonitrile-hydrogen-L(+)tartrate. Then it is neutralized with base to give the corresponding free base.

EXAMPLE 4

Resolution of Racemic 2-amino-2(4-methoxyphenyl)acetonitrile (Method B)

A solution of racemic 2-amino-2-(4-methoxyphenyl)acetonitrile (6 g; 0.037 mol) obtained as described in example 1 is added to a solution of L(+)tartaric acid (5.5 g; 0.037 mol) in methanol (20 ml) at 40° C. The mixture is stirred and after about 15 minutes a precipitate forms; the stirring is continued for 1 hour at 40° C., and then the mixture is cooled. The precipitate is collected by filtration, washed with methanol, and dried under reduce pressure. The obtained L(+)tartrate salt of the D(-)-2-amino-2-(4-methoxyphenyl)acetonitrile is transformed into the corresponding free base by neutralizing with base.

EXAMPLE 5

Recovery of the Starting Aldehyde Derivative by Hydrolyzing the Undesired Enantiomer of the 2-amino-2-(4-methoxyphenyl)acetonitrile.

L-2-amino-2-(4-methoxyphenyl)acetonitrile obtained by resolving the corresponding racemic mixture is dissolved in aqueous sodium hydroxide. After suitable stirring, 4-methoxybenzaldehyde is obtained. This product can be either further purified by column chromatography or used as such in the process of example 1.

WE CLAIM:

1. A process for preparing 2-amino-2-aryl-acetonitriles of formula I

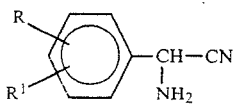

wherein R and R¹ independently represent hydrogen, hydroxy, hydroxy($C_1$-$C_4$)alkyl, ($C_1$-$C_4$)alkoxy, ($C_1$-$C_6$)alkyl, 2-furyl, 2-thienyl, 4-pyridyl, 1-pyrrolydinyl, 1-piperidinyl, 4-morpholinyl, 1-piperazinyl, 4-methyl-1-piperazinyl, 4-phenylpiperazinyl, phenyl optionally substituted with from 1 to 3 substituents selected from ($C_1$-$C_4$)alkyl and ($C_1$-$C_4$)alkoxy, or R and R¹ independently represent phenyl($C_1$-$C_4$)alkyl wherein the phenyl group can be substituted as above, which comprises:

(a) reacting an arylaldehyde of the following formula II

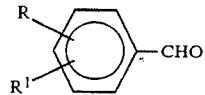

wherein R and R¹ are as above, with a molar excess of aqueous chloroform, optionally in the presence of a suitable organic solvent, under basic condition and in presence of an overpressure of ammonia;

(b) recovering the reaction product according to usual techniques.

2. A process as in claim 1 wherein the excess of chloroform is employed as the reactant as well as the reaction solvent.

3. A process as in claim 1 wherein the basic conditions are due to aqueous ammonia.

4. A process as in claim 1 wherein the basic conditions are obtained by using an aqueous alkali metal or alkali-earth metal hydroxide or aqueous alkali-metal carbonate.

5. A process as in claim 1 wherein the initial overpressure of ammonia is between 2 and 10 atm. at room temperature.

6. A process as in claim 1 wherein the reaction mixture is heated between 50° C. and 120° C.

7. A process as in claim 1 wherein the recovery of the reaction product is carried out by extracting the chloroform layer with aqueous acids.

8. A process as in claim 1 wherein the recovery of the reaction product is carried out by extracting the chloroform layer with hydrochloric acid.

9. A process as in claim 8 wherein the extracted acid aqueous layer is adjusted to a pH value between 7.2 and 8.0 and extracted with a suitable organic solvent.

10. A process as in claim 1 characterized in that the obtained racemic product is resolved into its enantiomers.

11. A process as in claim 1 characterized in that the obtained racemic product is resolved into its enantiomers and the undesired enantiomer is hydrolyzed in base to give the starting aldehyde derivative.

12. A process as in claim 1 characterized in that the obtained racemic product is resolved into its enantiomers and the undesired enantiomer is epimerized to transform it into the desired enantiomer.

13. A process as in claim 1 for preparing the compounds of formula I wherein R¹ is hydrogen and R is as defined with the exclusion of the meaning hydrogen.

14. A process as in claim 1 for preparing the compounds of formula I wherein R¹ is hydrogen and R is methoxy or benzyloxy.

15. A process as in claim 1 for preparing a compound which is 2-amino-2-(4-methoxyphenyl)acetonitrile.

* * * * *

UNITED STATES PATENT AND TRADEMARK OFFICE
CERTIFICATE OF CORRECTION

PATENT NO. : 4,487,721

DATED : December 11, 1984

INVENTOR(S) : Romeo Ciabatti

It is certified that error appears in the above-identified patent and that said Letters Patent is hereby corrected as shown below:

At column 2, lines 64-65, the patent reads "is remarkably lypophilic" and should read --is lypophilic-- as found in the specification at page 5, lines 3-4. At column 3, line 9, the patent reads "should be more with respect" and should read --should be more favourable with respect-- as found in the specification at page 5, line 17. At column 3, line 24, the patent reads "acid proven very" and should read --acid has proven very-- as found in the specification at page 5, line 34. At column 3, lines 36-37, the patent reads "chromatigraphic" and should read --chromatographic-- as found in the specification at page 6, line 13. At column 5, line 21, the patent reads "under reduce pressure" and should read --under reduced pressure-- as found in the specification at page 9, line 33.

Signed and Sealed this

Fourth Day of December, 1990

Attest:

HARRY F. MANBECK, JR.

Attesting Officer

Commissioner of Patents and Trademarks